US007609804B2

(12) United States Patent
Hoffman

(10) Patent No.: US 7,609,804 B2
(45) Date of Patent: Oct. 27, 2009

(54) CAST COLLIMATORS FOR CT DETECTORS AND METHODS OF MAKING SAME

(75) Inventor: David M. Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 84 days.

(21) Appl. No.: 11/552,477

(22) Filed: Oct. 24, 2006

(65) Prior Publication Data

US 2007/0064876 A1 Mar. 22, 2007

Related U.S. Application Data

(63) Continuation of application No. 11/533,611, filed on Sep. 20, 2006, which is a continuation of application No. 10/326,020, filed on Dec. 19, 2002, now abandoned.

(51) Int. Cl.
*A61B 6/03* (2006.01)

(52) U.S. Cl. ........................................ 378/19; 378/149

(58) Field of Classification Search .................. 378/19, 378/147, 149, 154

See application file for complete search history.

(56) References Cited

U.S. PATENT DOCUMENTS 3,585,387 A 6/1971 Bramlet
4,198,570 A 4/1980 McHugh et al.
4,277,685 A 7/1981 Covic et al.
4,748,328 A 5/1988 Chang et al.
5,528,655 A * 6/1996 Umetani et al. ............ 378/98.2
6,115,448 A * 9/2000 Hoffman ..................... 378/19
6,175,615 B1 1/2001 Guru et al.
6,275,568 B1 8/2001 Prins et al.
6,285,740 B1 9/2001 Seely et al.

(Continued)

FOREIGN PATENT DOCUMENTS

JP 60-144683 A 7/1985

(Continued)

OTHER PUBLICATIONS

Parallely vaned and channeled collimator/housing as depicted in this figure from Mikro Systems, Inc. of Charlottesville, VA.

*Primary Examiner*—Chih-Cheng G Kao
(74) *Attorney, Agent, or Firm*—Ziolkowski Patent Solutions Group, SC

(57) ABSTRACT

Cast collimators for use in CT imaging systems are described, as are methods of making them. Such collimators may comprise pre-patient collimators, pre-patient filter/collimator assemblies, and/or post-patient collimators. The filters and/or collimators may be made of any suitable high-density, high atomic number material such as lead, a lead alloy, tantalum, tungsten, tungsten suspended in an epoxy matrix, tungsten suspended in a slurry, or the like. Embodiments of these collimators comprise specially-designed channels and vanes that allow them to be precision cast to the necessary degree of accuracy. These channels and vanes are preferably tapered. These collimators and filter/collimator assemblies help minimize the x-ray dose to the patient by minimizing the scattered radiation creation mechanism and by collimating out much of the scattered radiation that would otherwise be subjected to the patient. These collimators may be cast as either single piece structures, or multiple pieces that can be operatively connected together.

22 Claims, 3 Drawing Sheets

U.S. PATENT DOCUMENTS

| | | | |
|---|---|---|---|
| 6,339,223 | B1 | 1/2002 | Motomura et al. |
| 6,365,900 | B1 | 4/2002 | Mestais et al. |
| 6,383,601 | B2 | 5/2002 | Prins et al. |
| 6,424,697 | B1 | 7/2002 | Zastrow et al. |
| 6,807,250 | B2 | 10/2004 | Wang et al. |
| 2004/0156478 | A1 * | 8/2004 | Appleby et al. ............. 378/147 |

FOREIGN PATENT DOCUMENTS

| | | | |
|---|---|---|---|
| JP | 05-071785 | U | 9/1993 |
| JP | 07-333395 | A | 12/1995 |
| JP | 10-268055 | A | 10/1998 |
| JP | 11-014758 | A | 1/1999 |
| WO | WO 0033058 | A2 * | 6/2000 |

* cited by examiner

CAST COLLIMATORS FOR CT DETECTORS AND METHODS OF MAKING SAME

CROSS REFERENCE TO RELATED APPLICATIONS

The present application is a continuation of and claims priority of U.S. Ser. No. 11/533,611 filed Sep. 20, 2006, which is a continuation of U.S. Ser. No. 10/326,020 filed Dec. 19, 2002, the disclosures of which are incorporated herein by reference.

FIELD OF THE INVENTION

The present invention relates generally to collimators for use in computed tomography (CT) imaging systems. More specifically, the present invention relates to cast collimators for use in CT imaging systems, and methods of making same. This invention also relates to filters for use with such collimators, and the choice of material(s) for making such filters and/or collimators.

BACKGROUND OF THE INVENTION

In CT imaging systems, pre-patient filters and collimators are used to shape an x-ray beam so that a fan-shaped x-ray beam lies within the X-Y plane, or the imaging plane, before its transmission through a patient. These pre-patient filters are generally used to shape the intensity of the x-ray beam in the X-direction, and are commonly enclosed in a housing (i.e., collimator) that determines the width of the x-ray beam in the Z-direction. The filtered and collimated x-ray beam is attenuated by the object being imaged (i.e., the patient having the CT scan performed on them), and the x-rays are then detected by an array of radiation detectors. Often times, the x-rays pass through a post-patient collimator prior to being detected by the array of radiation detectors. These post-patient collimators generally comprise a number of various parts that can be very difficult to accurately align and assemble.

The pre-patient collimators often generate significant scattered radiation that subjects the patient to x-ray dose that is not useful in the CT imaging process. Such scatter is becoming an increasing problem as CT manufacturers open up the fan-shaped x-ray beam more and more in the Z-direction to accommodate detectors with more slices and coverage in the Z-direction, thereby increasing the need for better pre-patient and post-patient collimator designs. As CT systems are becoming increasingly dose sensitive, it would be desirable to have systems and methods for making pre-patient filter/collimator assemblies that minimize the scattered radiation created therein and exiting therefrom so as to lower the x-ray dose the patient is exposed to.

The post-patient collimators are generally complicated structures comprising combs, rails, plates and wires. Currently, each comb must be attached to a rail, each plate must be individually inserted into appropriate slots in the combs and be attached thereto, and then wires must be individually strung and attached to the appropriate slots on each plate. This is a very time consuming, labor-intensive process, often requiring reworking if the components are not properly aligned. Therefore, it would be desirable to have systems and methods for making post-patient collimators in an easier, more efficient, and more economical manner than currently possible.

Filters used with such collimators could also be better designed to minimize the scattered radiation created therein and exiting therefrom so as to help further lower the x-ray dose the patient is exposed to.

It would be desirable to have collimators, both pre-patient and post-patient, that lower the x-ray dose the patient is exposed to by minimizing the scattered radiation created therein or exiting therefrom. It would be further desirable to have such collimators that can be more easily, more accurately, and more efficiently made than currently possible. It would also be desirable to have filters that minimize the scattered radiation created therein and exiting therefrom, for use in combination with such collimators, so as to help further reduce the x-ray dose the patient is exposed to. It would be still further desirable to have such filters and/or collimators be made of one or more cast pieces of a suitable high density, high atomic number material. Finally, it would be desirable to have such collimators to allow improved x-ray dose efficiency. Many other needs will also be met by this invention, as will become more apparent throughout the remainder of the disclosure that follows.

SUMMARY OF THE INVENTION

Accordingly, the above-identified shortcomings of existing systems and methods are overcome by embodiments of the present invention, which relates to collimators, both pre-patient and post-patient, that lower the x-ray dose the patient is exposed to by minimizing the scattered radiation created therein or exiting therefrom. Many embodiments of these collimators can be made more easily, more accurately, and more efficiently than currently possible. Embodiments of this invention also comprise filters that minimize the scattered radiation created therein and exiting therefrom, for use in combination with such collimators, so as to help further reduce the x-ray dose the patient is exposed to. Such filters and/or collimators are preferably made of one or more cast pieces of a suitable high density, high atomic number material. These collimators may allow improved x-ray dose efficiency to be achieved.

Embodiments of this invention comprise collimators for use in CT imaging systems. These collimators may comprise a two-dimensional honeycomb structure that comprises channels of a predetermined shape running between channel walls of a predetermined thickness. This two-dimensional honeycomb structure is preferably made via a casting process, and is capable of meeting predetermined precision requirements. When used as a pre-patient collimator, there may be a filter operatively coupled thereto, wherein the filter is preferably made of any high-density, high atomic number material such as lead, a lead alloy, tantalum, tungsten, tungsten suspended in an epoxy matrix, tungsten suspended in a slurry, or the like. The filter may be positioned in front of the collimator, or it may comprise a three-dimensional insert that is operatively positioned within the channels of the two-dimensional honeycomb structure. When used as a post-patient collimator, there may be channels running through the two-dimensional honeycomb structure. These channels could be of any shape, such as rectangular, circular, ovular, trapezoidal, hexagonal, square, or the like. Preferably, these channels are tapered to create a first aperture proximate an x-ray entry surface of the collimator that is larger than a second aperture proximate an x-ray exit surface of the collimator. The collimator itself may also be made of any high-density, high atomic number material such as lead, a lead alloy, tantalum, tungsten, tungsten suspended in an epoxy matrix, tungsten suspended in a slurry, or the like.

Other embodiments of this invention comprise filters for use in pre-patient filter/collimator assemblies in CT imaging systems, or for use in conjunction with post-patient collimators, if so desired. These filters preferably comprise any suitable high-density, high atomic number material that is capable of absorbing x-ray radiation, such as lead, a lead alloy, tantalum, tungsten, tungsten suspended in an epoxy matrix, tungsten suspended in a slurry, or the like.

Yet other embodiments of this invention comprise pre-patient filter and collimator assemblies for use in CT imaging systems. These assemblies may comprise: a filter component; and a collimator component, wherein the filter component is operatively coupled to the collimator component and the collimator component comprises a two-dimensional honeycomb structure comprising channels of a predetermined shape running between channel walls of a predetermined thickness. The filter and/or the collimator may be made of any suitable high-density, high atomic number material, such as lead, a lead alloy, tantalum, tungsten, tungsten suspended in an epoxy matrix, tungsten suspended in a slurry, or the like. The filter may be positioned in front of the collimator or anywhere else in suitable proximity to the collimator, or it may comprise a three-dimensional insert that is operatively positioned within the channels of the two-dimensional honeycomb structure.

Still other embodiments of this invention comprise post-patient collimators for use in CT imaging systems. These collimators preferably comprise: a two-dimensional honeycomb structure comprising channels of a predetermined shape running between channel walls of a predetermined thickness, wherein the two-dimensional honeycomb structure is capable of meeting predetermined precision requirements. Ideally, these collimators are made via a casting process. The channels in these collimators may comprise any suitable shape, such as rectangular, circular, ovular, trapezoidal, hexagonal, and/or square. Preferably, these channels are tapered to create a first aperture proximate an x-ray entry surface of the collimator that is larger than a second aperture proximate an x-ray exit surface of the collimator. The two-dimensional honeycomb structure may comprise any suitable high-density, high atomic number material, such as for example lead, a lead alloy, tantalum, tungsten, tungsten suspended in an epoxy matrix, tungsten suspended in a slurry, or the like.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DESCRIPTION OF THE DRAWINGS

The systems and methods of the present invention are described herein below with reference to various figures, in which.

DETAILED DESCRIPTION OF THE INVENTION

For the purposes of promoting an understanding of the invention, reference will now be made to some preferred embodiments of the present invention as illustrated in FIGS. 1-4, and specific language used to describe the same. The terminology used herein is for the purpose of description, not limitation. Specific structural and functional details disclosed herein are not to be interpreted as limiting, but merely as a basis for the claims as a representative basis for teaching one skilled in the art to variously employ the present invention. Any modifications or variations in the depicted support structures and methods of making same, and such further applications of the principles of the invention as illustrated herein, as would normally occur to one skilled in the art, are considered to be within the spirit of this invention.

Figure 1:
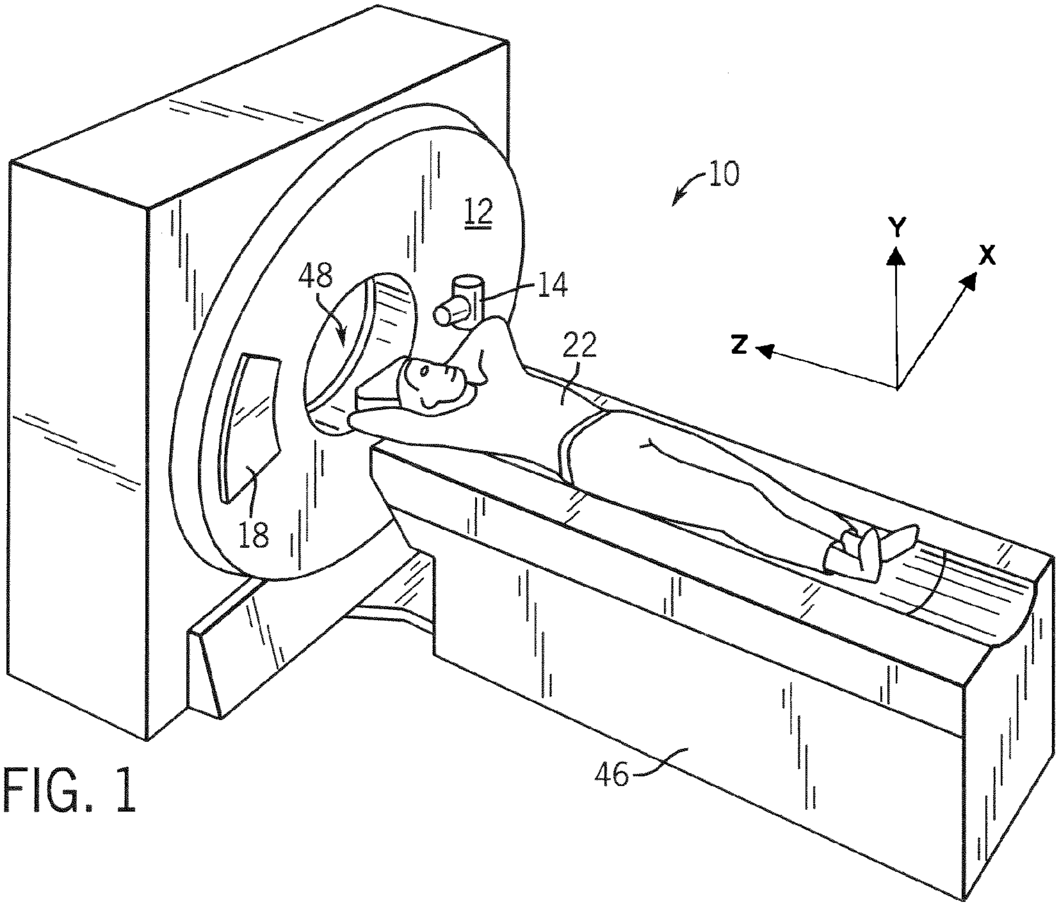
FIG. 1 is perspective view of an exemplary CT imaging system.
Figure 2:
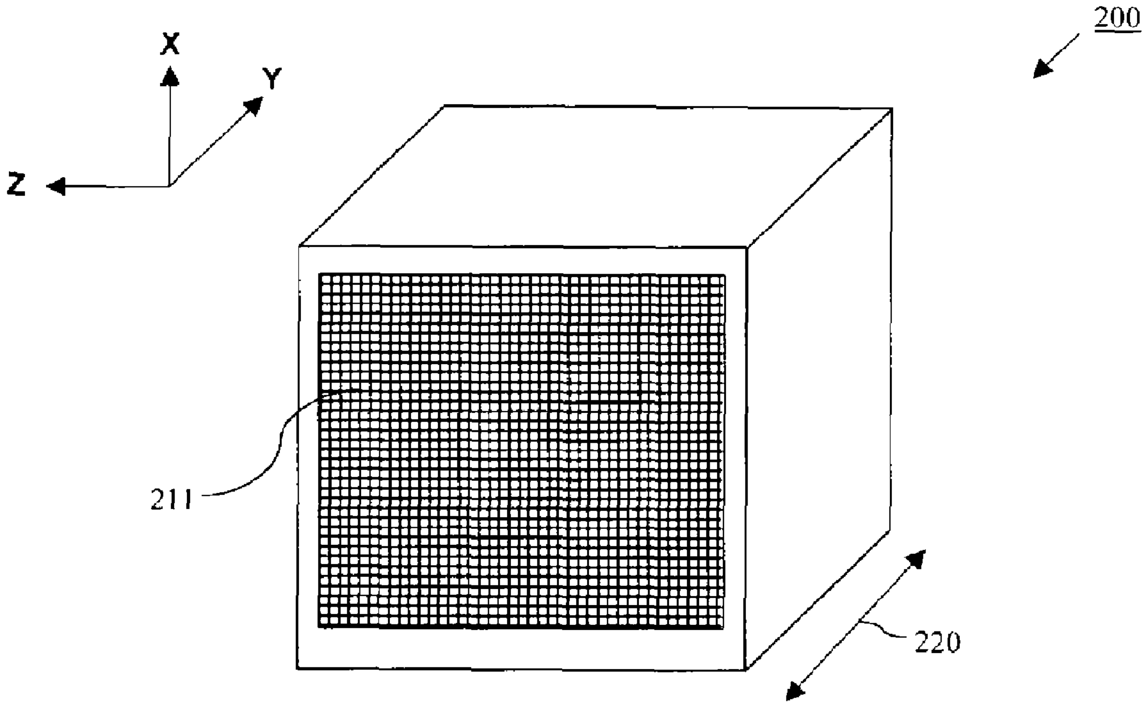
FIG. 2 is a perspective view of a high aspect ratio pre-patient collimator as utilized in embodiments of this invention.

FIG. 1 shows an exemplary CT imaging system 10. Such systems generally comprise a gantry 12, a gantry opening 48, and a table 46 upon which a patient 22 may lie. Gantry 12 comprises an x-ray source 14 that projects a beam of x-rays 16 toward an array of detector elements 18. Generally, the array of detector elements 18 comprises a plurality of individual detector elements that are arranged in a side-by-side manner in the form of an arc that is essentially centered on x-ray source 14. In multi-slice imaging systems, parallel rows of arrays of detector elements 18 can be arranged so that each row of detectors can be used to generate a single thin slice image through patient 22 in the X-Y plane. Each detector element in the array of detector elements 18 senses and detects the x-rays 16 that pass through an object, such as patient 22. While this figure shows the x-ray source 14 and the array of detector elements 18 aligned along the X-axis, some CT imaging systems may align the x-ray source 14 and the array of detector elements 18 differently, such as along the Y-axis or anywhere else in the X-Y plane.

In many CT imaging systems, pre-patient filters and collimators are utilized between x-ray source 14 and patient 22 to shape the x-ray beam 16 coming from x-ray source 14 before its transmission through patient 22. The filters in these assemblies tend to shape the intensity of the x-ray beam in the X-direction across the patient 22, and are commonly enclosed in a housing that determines the width of the x-ray beam in the Z-direction. Generally, the housing collimation in Z is achieved by using adjustable collimator blades or jaws to adjust the total area exposed in Z. However, one major drawback to current pre-patient filter/collimator assemblies is that they often generate significant scattered radiation that subjects the patient to x-ray dose that is not useful in the CT imaging process. As previously mentioned, scatter is becoming an increasing problem as CT manufacturers open up the fan-shaped x-ray beam more and more in the Z-direction to accommodate detectors with more slices and coverage in the Z-direction, thereby increasing the need for better pre-patient and post-patient collimator designs. The increase in such scatter seems to be linear with the increase in the Z-direction beam width. As CT imaging systems become more and more dose sensitive, it would be desirable to have pre-patient filter/collimator assemblies that minimize the scattered radiation created therein or exiting therefrom, so as to lower the x-ray dose the patient 22 is exposed to. This invention may reduce the scattered x-ray radiation creation mechanism in pre-patient filter/collimator assemblies, as well as provide for the collimation and subsequent minimization of the scattered radiation that is created therein.

Utilizing specific materials for the filters in these pre-patient filter/collimator assemblies may help minimize the scattered radiation generated within the pre-patient filter/collimator assemblies. Typically, these filters are made of plastics, Teflon®, Flexan® and/or other low density, low atomic number materials that have a high Compton to total cross section ratio (i.e., their primary attenuation mechanism is via scattering, not via photo-electric absorption). Choosing materials for the filters that have a high photo-electric to total cross section ratio may help minimize the radiation scattered within the filter by reducing or eliminating the scattered radiation creation mechanism. Such materials may include any high atomic number, high density material that is good for absorbing x-rays to minimize x-ray scatter, such as for example, lead, a lead alloy, tantalum, tungsten, tungsten suspended in an epoxy matrix, tungsten suspended in a slurry, or any other high density, high atomic number material that is capable of optimizing X-ray absorption. The collimators may also benefit from being made from the same high density, high atomic number materials as the filters. The filters and collimators may comprise a single material, a stack of materials, or a composite material.

The pre-patient scattered radiation could be further reduced by positioning a honeycomb-shaped collimator 200 proximate a filter, to filter out even more of the scattered radiation, especially the forward scattered radiation that is directed at the patient. Such a structure may be highly desirable since the pre-patient filter/collimator assemblies currently available do not have much of an aspect ratio, thereby allowing significant quantities of forward scattered radiation to escape and be subjected to the patient. In preferred embodiments, this pre-patient filter/collimator assembly may comprise utilizing a three-dimensional insert in the Z-slice width collimator that has small holes in it, which effectively acts as a high aspect ratio collimator to absorb the scattered radiation that may be generated in the filter positioned in front of the pre-patient collimator. Such an assembly would preferably be made by a casting process, which would allow honeycomb structures having very thin walls or vanes to be made. High density, high atomic number materials could be used to make such honeycomb structures to further help minimize the scattered radiation, and thereby reduce the x-ray dose to the patient.

In embodiments, the filter material could be positioned within the honeycomb structure itself, similar to honey in a honeycomb. In yet other embodiments, instead of casting these pre-patient collimators, stacked etched foils could be used, or plate-plate egg crate assemblies could be used.

In one preferred embodiment, the pre-patient filter/collimator assemblies comprise a specially-selected, high atomic number, high density material for the filter, and a high aspect ratio collimator having small channels therein operatively coupled to the filter. This collimator 200 may comprise a cast 2-dimensional honeycomb structure, such as that shown in FIG. 2, where the honeycomb structure comprises small rectangular-shaped channels 211 running throughout the depth 220 of the collimator 200. Casting such a structure is preferable because it allows small apertures in between very thin walls to be created. It will be apparent to those skilled in the art that there are numerous other suitable ways to make such a structure, such as by stacking etched foils, using plate-plate egg crate assemblies, and the like, and all such variations are deemed to be within the scope of this invention. These cast structures may comprise a single cast piece, or multiple cast pieces that may be joined together. As is well known to those skilled in the art, all pre-patient and post-patient collimators comprise radial assemblies that are focused at the x-ray tube focal spot.

Many CT imaging systems also utilize post-patient collimators between the patient 22 and the array of detector elements 18 to focus the attenuated x-rays 16 that pass through patient 22 onto the various detector elements in the array of detector elements 18. Current post-patient collimators comprise numerous precision or semi-precision machined or fabricated parts that must be precisely positioned and assembled, one at a time, by hand. As evidenced by the fact that some current post-patient collimators comprise as many as 2 rails, 2 combs that must each be attached to a rail, 944 plates that must be individually inserted into appropriate slots in the combs and be attached thereto, and 17 tungsten wires that must be individually strung and attached to the appropriate slots on each plate, this is a very labor-intensive, time consuming process. Therefore, it would be desirable to have systems and methods for making such collimators in an easier, more efficient, and more economical manner than currently possible.

The post-patient collimators of this invention are preferably made via casting, which allows thin, tapered vanes to be created, thereby reducing non-linearities and image artifacts commonly caused by misaligned collimator vanes in existing post-patient collimators. Non-linearities in existing post-patient collimators may be caused when the x-ray source moves slightly during operation, as is common due to the heat generated by the rotating anode within the x-ray generation source, thereby causing the x-ray beams to be aligned in a non-parallel manner with respect to the channels in the collimator, resulting in shadowing at the x-ray exit surface 215 of the collimator. Such non-linearities are often corrected in existing post-patient collimators by skewing the vanes to slightly misalign the plates in the collimator; this greatly reduces the channel-to-channel nonlinearities induced by focal spot motion of the x-ray beam during operation. Casting these post-patient collimators may help improve x-ray dose utilization and efficiency by allowing thinner, tapered vanes to be used therein, thereby eliminating the need to skew the vanes. It would be almost inconceivable to create tapered vanes in any manner other than casting.

While cast collimator assemblies are currently utilized in nuclear and/or gamma camera systems, such collimators are not as accurate as those needed for CT collimators, nor are they thin-walled structures. However, recent advances in casting technology have made casting more attractive for the manufacture of low-cost precision CT collimators. The casting process lends itself to some novel advantages when applied to the manufacture of CT collimators, for both pre-patient and post-patient collimators. Casting allows collimators having very thin walls with very small channels or apertures therebetween to be formed. Casting also allows tapered vanes to be created in such collimators. For example, in the honeycomb structure described above in pre-patient collimators, the channels were merely rectangular-shaped channels 211 in the imaging plane. However, by utilizing casting technology, it may be possible to form tapered channels of varying shapes in both pre-patient and post-patient collimators, if tapering is so desired.

Figure 4:
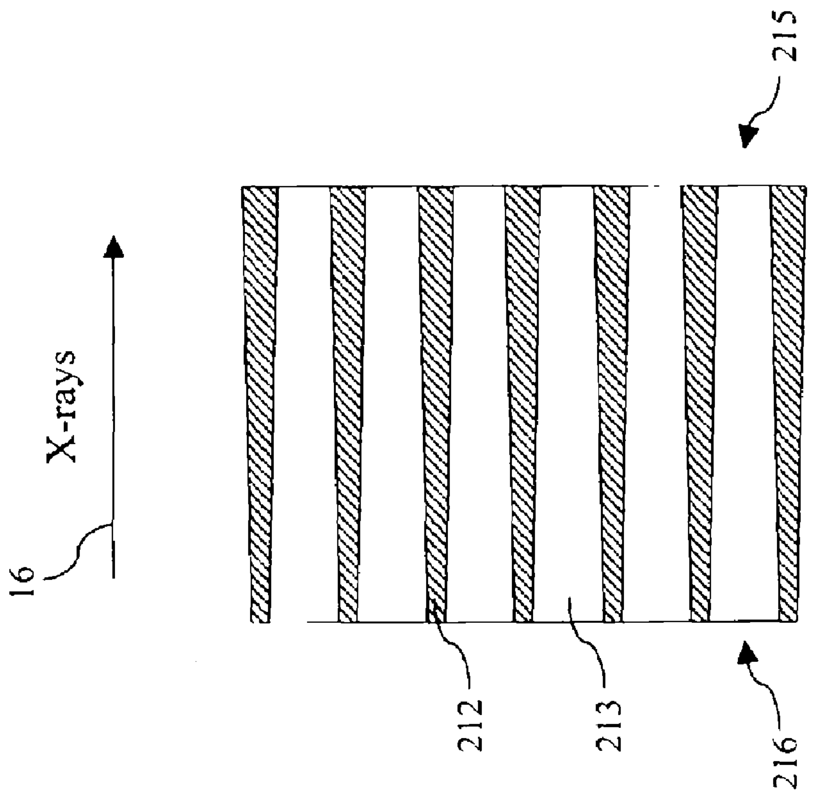
FIG. 4 is a portion of a cross-sectional side view showing some 2-dimensionally tapered, trapezoidal-shaped vanes and channels as cast in other embodiments of this invention.
Figure 3:
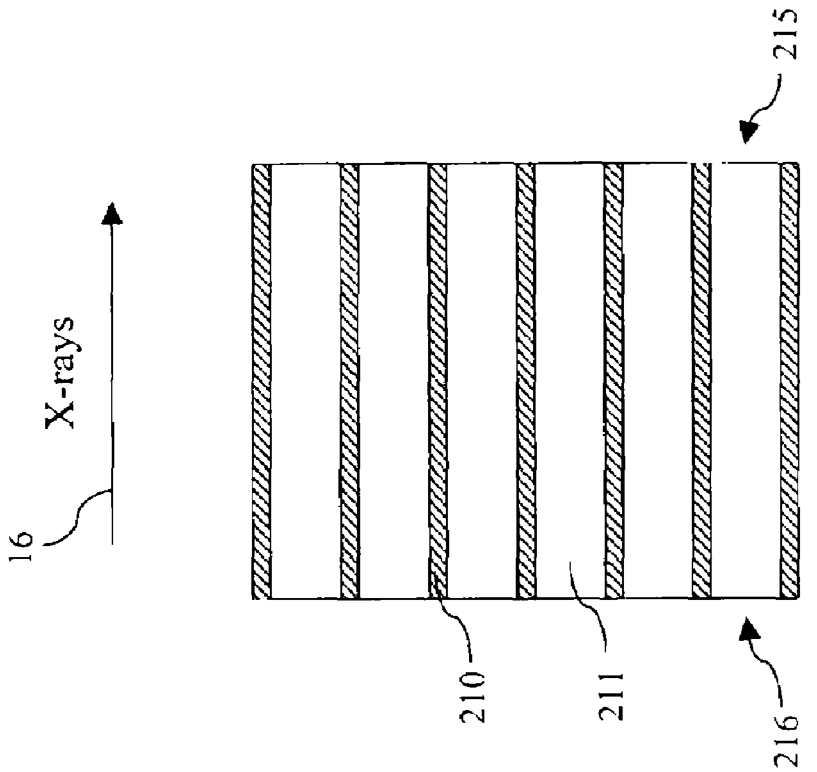
FIG. 3 is a portion of a cross-sectional side view showing some non-tapered, rectangular-shaped vanes and channels as cast in embodiments of this invention.

These cast channels could be tapered in one dimension or two, whichever is desired. For example, these channels may be tapered in only the X-direction or the Y-direction (i.e., 1-D taper), or they could be tapered in both the X-direction and the Y-direction (i.e., 2-D taper). While many embodiments utilize rectangular-shaped vanes and channels, casting allows various other shaped vanes and channels to be formed therein, such as for example round channels or hexagonal channels, both of which could also be tapered in one dimension or two, whichever may be desired. A portion of a cross-sectional side view showing some non-tapered, rectangular-shaped vanes 210 and rectangular-shaped channels 211, as cast in embodiments of this invention, can be seen in FIG. 3. A portion of a cross-sectional side view showing some tapered, trapezoidal-shaped vanes 212 and trapezoidal-shaped channels 213, as cast in other embodiments of this invention, is shown in FIG. 4. It will be apparent to those skilled in the art that numerous other shaped channels could be created in these collimators, and all such variations are deemed to be within the scope of this invention.

Tapering the vanes in these post-patient collimators allows the exacting precision required of such collimators to be required on only one surface of the collimator, for example, on the x-ray exit surface 215, but not on the x-ray entrance surface 216. If the vanes are tapered in such collimators, the non-precision surface of such collimators (i.e., the x-ray entrance surface 216), may be hidden behind or within the shadow of the precision surface (i.e., the x-ray exit surface 215), thereby reducing the need for precision accuracy on both surfaces since the shadow created by the non-precision surface can move around a bit as long as it stays within the shadow created by the precision surface. As creating precision dimensions on only one surface is much easier than creating precision dimensions on multiple surfaces, this greatly improves the probability of being able to apply the much more cost effective casting technology to the manufacture of CT collimators. Tapering the vanes may also eliminate the varying shadowing effects that are commonly caused by misaligned collimator vanes in existing post-patient collimators. Furthermore, tapering the vanes eliminates the need to skew the vanes, as is commonly done in existing post-patient collimators to improve x-ray dose efficiency.

While tapering these vanes and channels provides many advantages, the vanes and channels in these pre-patient and post-patient collimators do not have to be tapered. Furthermore, the honeycomb structure of these collimators can be made with 2-dimensional septa, 1-dimensional septa, or the equivalent of the current plates and wires used in such collimators. As will be apparent to those skilled in the art, numerous cast designs of these collimators are possible. The collimators may be cast as single piece structures, or they may be cast as multiple pieces that are capable of being operatively coupled together.

As described above, the systems and methods of the present invention allow both the pre-patient and post-patient collimators to be made via a casting process, allowing very accurate collimators to be made much easier and more economically than currently possible. Advantageously, these collimators also help minimize scattered x-ray radiation, thereby reducing the x-ray dose that patients are exposed to. The materials selected for making such collimators may help minimize the scattered radiation that is being created within such collimator assemblies or scattered therefrom, and the honeycomb structures may help further reduce the scattered radiation that patients are subjected to. This is particularly advantageous since CT imaging systems are becoming more dose sensitive, and it is desirable to expose the patient to no more radiation than necessary.

Various embodiments of this invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. For example, while tapered vanes are described in relation to cast post-patient collimators, they could also be used in cast pre-patient collimators if desired. Thus, it is intended that the present invention cover all suitable modifications and variations as come within the scope of the appended claims and their equivalents.

What is claimed is:

1. An imaging system comprising:

an x-ray tube configured to emit x-rays toward a subject;

a CT detector positioned to receive the x-rays; and an assembly positioned between the subject and the CT detector, the assembly comprising a two dimensional array of channels which collimate the x-rays, the channels having walls that taper along an axis to coincide with that of the x-rays, the tapered walls increasing in thickness in a direction parallel with a direction of the x-rays such that at least one channel of the array of channels comprises a first aperture proximate an x-ray entry surface of the assembly that is larger than a second aperture proximate an x-ray exit surface of the assembly.

2. The imaging system of claim 1 wherein the first aperture is larger than the second aperture in both an x and z dimension of the CT system.

3. The imaging system of claim 1 wherein the two dimensional array of channels converges at a focal spot of the x-ray tube.

4. The imaging system of claim 1 wherein the assembly comprises a material having a density and atomic number similar to or higher than tungsten.

5. The imaging system of claim 4 wherein the material is of a density and atomic number that is sufficient to substantially attenuate x-rays.

6. The imaging system of claim 4 wherein the material comprises at least one of lead, a lead alloy, tantalum, tungsten, tungsten suspended in an epoxy matrix, and tungsten suspended in a slurry.

7. The imaging system of claim 1 wherein the two dimensional array of channels are one of rectangular, circular, and hexagonal shaped.

8. The imaging system of claim 1 wherein the assembly is constructed as a unitary one-piece material.

9. The imaging system of claim 1 wherein the x-ray exit surface has a precision that is greater than a precision of the x-ray entry surface.

10. The imaging system of claim 1 further comprising a stack of at least two materials which form the collimator.

11. A CT imaging system comprising:

a gantry;

an x-ray tube having a focal spot, the x-ray tube positioned on the gantry;

a detector positioned on the gantry opposite the x-ray tube; and a collimator having a two-dimensional array of collimating elements positioned between a subject and the detector, the collimator having a series of channels formed by tapered walls, wherein a thickness of the walls increases in a direction toward the detector such that at least one channel of the series of channels includes a first aperture proximate an x-ray entry surface of the collimator that is larger than a second aperture proximate an x-ray exit surface of the collimator.

12. The CT imaging system of claim 11 wherein the collimator has a series of channels aligned with x-rays that emit from the x-ray tube, the series of channels formed by tapered walls, wherein the taper of the walls increases in width in a direction parallel with a direction of the x-rays.

13. The CT imaging system of claim 12 wherein the series of channels are each focused at the focal spot of the x-ray tube.

14. The CT imaging system of claim 12 wherein the series of channels generally forms a honeycomb structure.

15. The CT imaging system of claim 11 wherein the collimator is formed of a material having a density and atomic number similar or higher than tungsten.

16. The CT imaging system of claim 15 wherein the material comprises at least one of lead, a lead alloy, tantalum, tungsten, tungsten suspended in an epoxy matrix, and tungsten suspended in a slurry.

17. The CT imaging system of claim 15 wherein the material has a density and atomic number high enough to substantially attenuate x-rays that pass through it.

18. A method of fabricating a collimator for a CT medical imaging system, the method comprising:

providing a material having a density and atomic number similar or higher than tungsten; and casting the material to form a two dimensional array of a plurality of channels having a taper and a plurality of vanes having a taper, wherein the taper of each vane positioned between adjacent channels tapers in a direction opposite that of a direction of the taper of the adjacent channels.

19. The method of claim 18 wherein a width of the plurality of channels narrows in a direction of unscattered x-ray travel through the plurality of channels.

20. The method of claim 18 wherein the plurality of channels is focused at a focal spot of an x-ray tube.

21. The method of claim 18 wherein the material is sufficiently dense to substantially attenuate x-rays.

22. The method of claim 18 wherein the material comprises one of lead, a lead alloy, tantalum, tungsten, tungsten suspended in an epoxy matrix, and tungsten suspended in a slurry.

* * * * *